Figure 1:
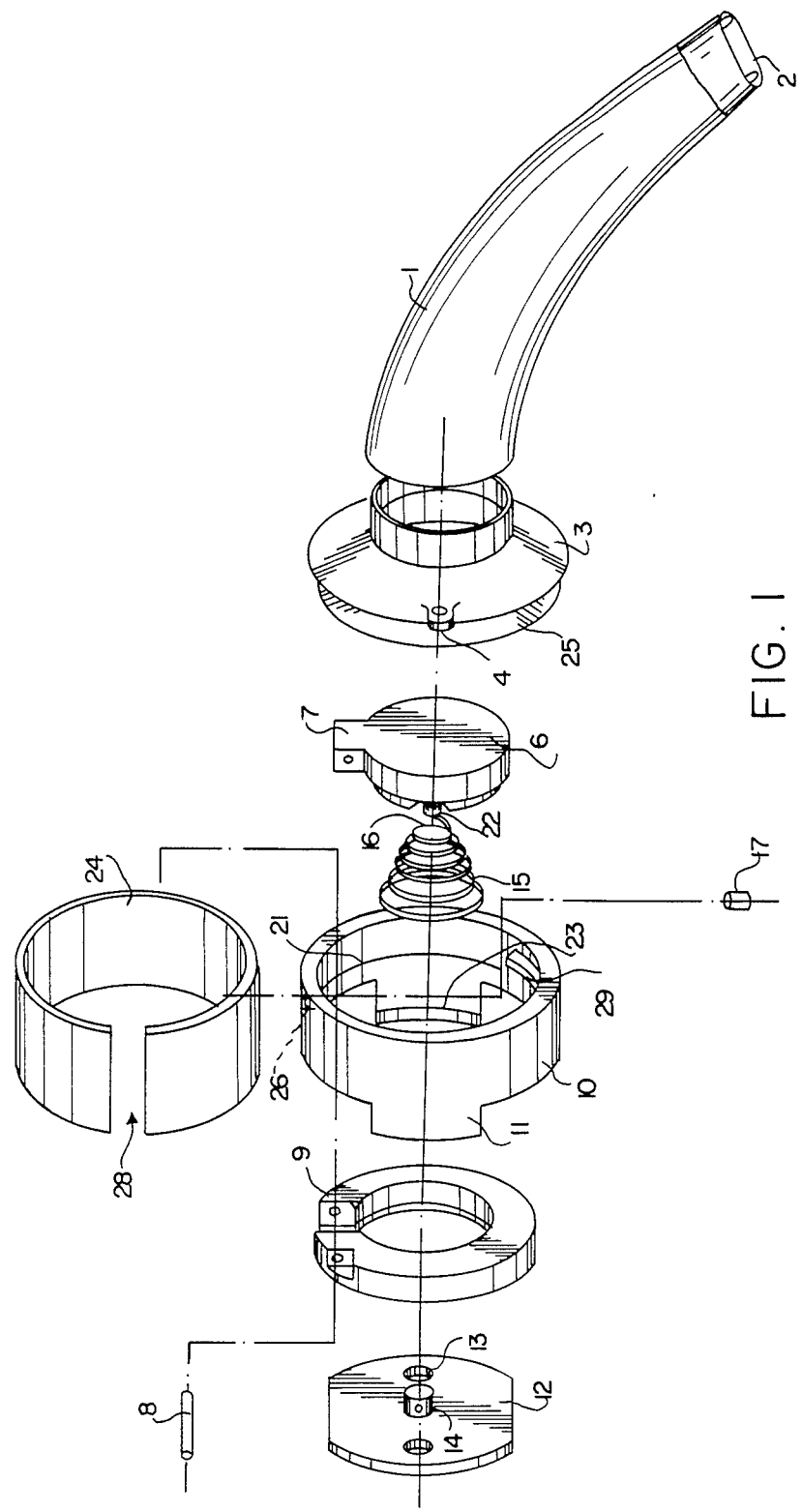

United States Patent [19]

Rangoni et al.

[11] Patent Number: 4,809,693
[45] Date of Patent: Mar. 7, 1989

[54] TRACHEAL INTUBATION CANNULA WITH EXTERNAL VALVE

[76] Inventors: Marco Rangoni, Via delle Fragole, 45, Bologna; Roberto Rangoni, Via Venezia, 20, S. Lazzaro Savena (Bologna); Dante Cavalli, Via Dell'Artigiano, 9; Walter Cavalli, Via Dell'Artigiano, 11, both of Villanova Castenaso (Bologna), all of Italy

[21] Appl. No.: 75,106

[22] Filed: Jul. 20, 1987

Related U.S. Application Data

[63] Continuation-in-part of Ser. No. 820,713, Jan. 17, 1986, abandoned, which is a continuation-in-part of Ser. No. 563,665, Dec. 20, 1983, abandoned.

[30] Foreign Application Priority Data

Dec. 22, 1982 [IT] Italy .................................. 3631 A/82

[51] Int. Cl.4 .............................................. A61M 16/00
[52] U.S. Cl. ...................................... 128/207.16; 623/9
[58] Field of Search ....................... 128/200.26, 207.14, 128/207.15, 207.17, 305.3, 205.25, 207.16; 623/9, 247; 137/527

[56] References Cited

U.S. PATENT DOCUMENTS

| | | | |
|---|---|---|---|
| 1,615,718 | 1/1987 | Olgard | 128/205.24 |
| 2,039,142 | 4/1936 | Brehm | 128/207.16 |
| 2,804,076 | 8/1957 | Girandon | 128/207.16 |
| 3,370,305 | 2/1968 | Gooh et al. | 137/527 |
| 3,606,669 | 9/1971 | Kemble | 128/200.26 |
| 3,683,931 | 8/1972 | Chelucci et al. | 128/207.16 |
| 3,952,335 | 4/1976 | Sorce et al. | 623/9 |
| 4,040,428 | 8/1977 | Clifford | 128/207.18 |
| 4,203,150 | 10/1980 | Scaramucci | 137/527 |
| 4,315,555 | 2/1982 | Crandall et al. | 128/200.26 |
| 4,325,366 | 4/1982 | Tabor | 128/207.16 |
| 4,538,607 | 9/1985 | Saul | 623/9 |

FOREIGN PATENT DOCUMENTS

| | | | |
|---|---|---|---|
| 2513113 | 3/1983 | France | 623/9 |
| 137230 | 8/1959 | U.S.S.R. | 623/9 |

Primary Examiner—Edward M. Coven
Assistant Examiner—K. M. Reichle
Attorney, Agent, or Firm—Collard, Roe & Galgano

[57] ABSTRACT

This invention relates to a cannula for tracheal intubation, inserted through the hole made in the trachea of the patient. The cannula is fitted at the top with a mechanically operated valve which remains open during normal breathing but which can close and consequently interrupt the flow of air to the outside when the patient, in order to direct the air towards the vocal cords, breathes out with greater force, sufficient to overcome the resistance of the spring within the valve.

8 Claims, 2 Drawing Sheets

TRACHEAL INTUBATION CANNULA WITH EXTERNAL VALVE

This is a continuation-in-part application of U.S. Ser. No. 820,713, filed Jan. 17, 1986, which in turn is a continuation-in-part application of U.S. Ser. No. 563,665, filed Dec. 20, 1983, both now abandoned.

This invention relates to a tracheal tube fitted with a mechanically operated valve intended specifically for patients who have undergone a tracheotomy, especially where it is impossible to rebuild the upper airways and where consequently the tracheostomy must be maintained. It is known that by means of this procedure the air enters the lungs via the opening made in the trachea and is expelled by the same route, thus bypassing the upper airways. This procedure obviously does not give the patient any possibility of speech. It is also known that these patients, in order to produce any vocal sounds, must manually close off the opening in the trachea, thus directing the flow of air over the vocal cords (if these are still present). The present invention overcomes this main disadvantage by means of a valve fixed to the external end of the tube. This valve is able to interrupt the outflow of air depending on the force with which this air is expelled. The present invention also reduces other problems found with traditional tracheostomy tubes without valves, such as the very high possibility of bacterial contamination while, in cases where a simpler valve is fitted, this invention also manages to overcome (by means of a spring-clip) the problem of quick valve replacement. To date, this is a problem common to all commercially available endotracheal tubes and is important given the fact that the valves tend to become blocked with pulmonary secretions.

The above and other objects are achieved by the device which is the subject of this invention, and which is essentially characterized as consisting of a tracheostomy tube measuring 5-6 cms, slightly bent, shaped in such a way as to facilitate entry of the lower extremity through the tracheal opening, that is, it reduces in diameter and has a rounded end. The top extremity has a small collar suitably shaped to fit over the opening in the neck without causing irritation due to the unavoidable movement that occurs between the parts in contact. At the same time, this collar provides the recess for the valve, which is fitted to it by means of a spring-clip. The valve consists of a cylindrical body ending with two projections at the ends of which is fixedly secured a top plate which has an area less than that of the cylinder end. Inside the cylinder body is a fixedly secured circular ring which acts as the valve seat and which is prevented from unwanted movement by means of a projecting ridge in the cylinder body.

The said valve is kept open by a spiral compression spring placed between the valve opening and the top plate; the top plate has a central stud with a hole through it, which together with a second similar stud placed at the center of the valve flap keeps the two ends of the spring in place by engagement with said holes. The top plate can have holes drilled in it to facilitate the passage of air, or else in order to enable a covering ornamental medallion (which would disguise the endotracheal tube opening) to be fixed to it by means of screws. To this end two supporting rings are provided on the collar to enable a chain (which would go around the patient's neck) to be fitted—this chain completes the ornamental effect but much more importantly prevents the tube from accidentally falling down to the floor.

These and other characteristics will now be described in greater detail using a simple example of the device which is however intended to be purely illustrative and does not limit in any way the scope of this invention.

Figure 2:
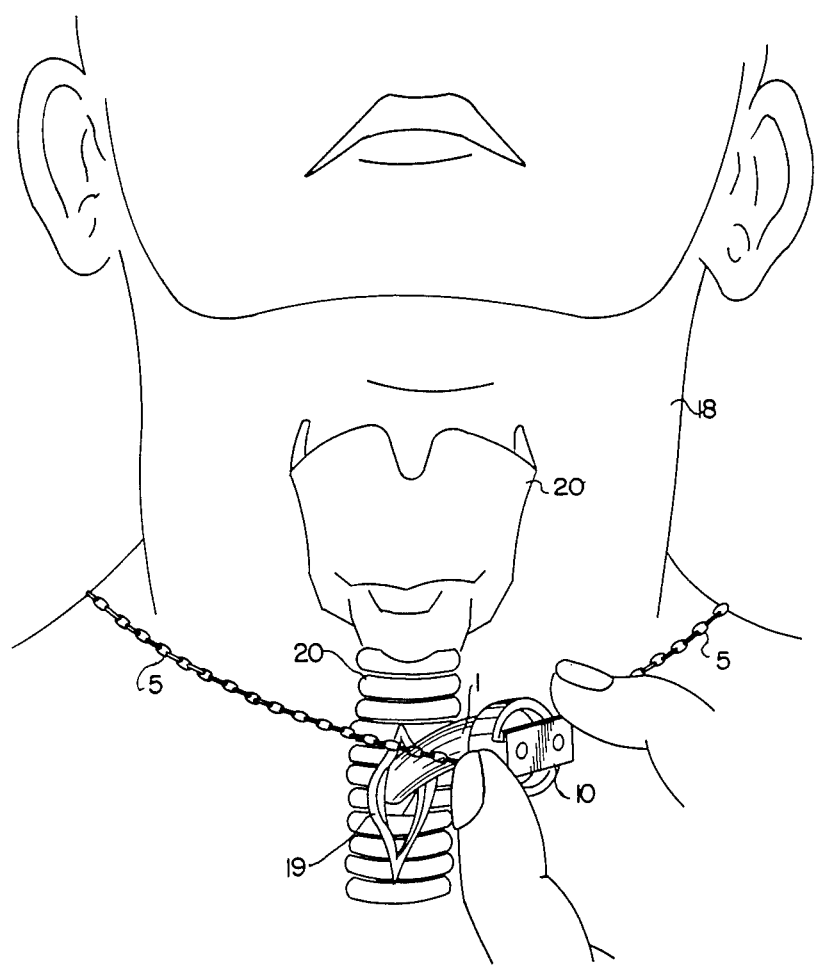

In the drawings wherein similar reference characters denote similar elements throughout the several views:

FIG. 1 is an exploded perspective view of the tracheal tube according to the present invention; and FIG. 2 is a view showing the tracheal tube inserted in a patient.

Now turning to FIGS. 1 and 2 of the drawings, 1 shows the cannula formed of biocompatible material such as plastic or metal, 2 is the rounded inner edge, 3 is the collar, shaped so as to achieve a non-irritant contact, 4 are the rings to which the chain 5 is attached. Numeral 6 designates the disc-shaped valve flap, 7 is the projection for the pin 8 which joins the valve flap to its seat 9 which is fixedly secured as by being press fit or frictionally held in outer casing 10 of the valve while 11 are the projections to which the top plate 12 is fixed. Top plate 12 is frictionally held between projections 11 wherein a ridge 23 prevents the inadvertent movement of plate 12 towards cannula 1. Numerals 13 designate the holes (intended for a number of uses) drilled in the top plate, numeral 14 is the central perforated stud which takes one end of the compression spring while the other end 16 is kept in place by a similar stud, designated 22 located at the center of the valve flap. Ridge 21 on the inside of casing 10 supports valve seat 9 and prevents inadvertent movement towards cannula 1. Numeral 17 designates the pawl of the release mechanism, which includes spring clip 24. Spring clip 24 fits around valve body 10 and maintains pawl 17, which projects through hole 26 in valve body 10, in frictional engagement with flared flange 25 of collar 3 and secured in said position by a second inward projection 29, opposite hole 26, which acts against flared flange 25 of collar 3. Said projection is introduced into flared flange 25 before the mounting of pin 17 that is in turn locked in place by spring clip 24 set around valve body 10 so as to prevent opening 28 from coinciding with hole 26 and pin 17 from moving out of place. By rotating spring clip 24 to align slot 28 thereof with pawl 17, the engagement with flared flange 25 is released and the valve may then be disengaged from collar 3. In FIG. 2, 18 is the neck of the patient on whom a tracheostomy 19 has been carried out, while 20 shows the trachea. The various elements of the device, apart from the cannula 1 are formed of metal.

The device operates as follows: during respiration the patient breathes in air through the valve which is kept open by the spring and the following expiration is always through the same opening so that air from the lungs does not reach the upper airways. During speech the patient, by emitting the air with greater force, overcomes the pressure exerted by the spring and thus closes the valve. Hence the air, since it cannot escape through the tracheostomy opening, is directed upwards thus reaching the vocal cords. It is also possible for the patient to regulate the closing pressure of the valve by providing a movable top plate 12 which can be moved to regulate the spring pressure of the spring.

In practice, details of production, dimensions and materials, the shape and other details of the device can be varied without departing from the scope of the present invention. In fact the device, as conceived, can undergo numerous modifications and variations, all of which however keep the device within the scope of the invention as originally conceived. Additionally, all the component parts are replaceable by other technically equivalent component parts.

What is claimed is:

1. A tracheal intubation cannula with external valve for permitting speech, comprising:
   (a) a cannula having an end adapted to extend into the trachea of a patient and a free end;
   (b) means for detachably mounting said valve to the free end of said cannula;
   (c) a cylindrically-shaped valve body open at its ends and mounted at one end to the free end of said cannula by said mounting means, said valve body including an annular ridge on the interior thereof facing away from said cannula;
   (d) a substantially circular valve seat mounted within said valve body and supported on the annular ridge thereof so as to prevent inadvertent movement of said valve seat towards said cannula, said valve seat having two ends defining a slot extending therethrough;
   (e) a valve flap adapted to cooperate with said valve seat to effect sealing against a side of said valve seat facing said cannula, said valve flap having a peripheral extension formed to extend into the slot on said valve seat and having a stud formed on the side face of said valve flap facing away from said cannula and having a transverse hole therethrough;
   (f) a hinge pin extending through the slot in said valve seat and the peripheral extension of said valve flap so as to hingedly connect said valve flap to said valve seat so that said valve flap is adapted to open to a position toward said cannula and to close to a position sealed against the side of said valve seat facing said cannula;
   (g) a top plate mounted to the remaining open end of said cylindrically-shaped valve body shaped so as to permit air to pass thereby into said valve body, said top plate having a stud formed at the interior surface thereof having a transverse hole therethrough; and
   (h) a compression type spiral spring having transverse free ends received in the holes of said studs of said top plate and said valve flap, said spring biasing said valve flap to a normally open position toward said cannula permitting atmospheric communication therethrough with said cannula, the bias of said spring being overcome by predetermined positive pressure exerted through said cannula so as to close said valve flap on said valve seat.

2. The valve as defined in claim 1, wherein the cannula is slightly bent and is of reducing cross-section as it approaches the end extending into the trachea, and the edges of said end are rounded to facilitate easy introduction of the cannula into the trachea.

3. The valve as defined in claim 1, which further includes rings provided on the exterior thereof and a supporting chain attached thereto.

4. The valve as defined in claim 1, wherein said top plate is provided with openings therein to improve air flow.

5. The valve as defined in claim 1, wherein the cannula is formed of plastic and the valve is formed of metal.

6. The valve as defined in claim 1, wherein the cannula is formed of metal and the valve is formed of metal.

7. The valve as defined in claim 1, wherein for securement of a covering ornament thereto said top plate is provided with openings therein.

8. The valve as defined in claim 1, wherein said means for detachably mounting said valve to the free end of said cannula comprises:
   (a) a flared flange at the free end of said cannula adapted to extend into said valve body;
   (b) a pin receiving opening in said valve body adjacent the position of said flared flange when extending into said valve body;
   (c) a pin received in said pin opening and extending into said valve body to engage said flared flange;
   (d) a spring clip having a longitudinal slot therein extending around said valve body to hold said pin against said flared flange; and
   (e) a projection in said valve body opposite said pin receiving opening which extends into engagement with said flared flange of said cannula.

* * * * *